US007632233B2

(12) United States Patent
Satoh et al.

(10) Patent No.: US 7,632,233 B2
(45) Date of Patent: Dec. 15, 2009

(54) ULTRASONIC ENDOSCOPE AND ULTRASONIC ENDOSCOPIC APPARATUS

(75) Inventors: Yoshiaki Satoh, Kaisei-machi (JP); Kazuhiro Tsujita, Kaisei-machi (JP)

(73) Assignee: FUJIFILM Corporation, Tokyo (JP)

( * ) Notice: Subject to any disclaimer, the term of this patent is extended or adjusted under 35 U.S.C. 154(b) by 555 days.

(21) Appl. No.: 11/206,168

(22) Filed: Aug. 18, 2005

(65) Prior Publication Data
US 2006/0058679 A1  Mar. 16, 2006

(30) Foreign Application Priority Data
Aug. 20, 2004   (JP) ............................. 2004-240787

(51) Int. Cl.
*A61B 8/14* (2006.01)
*H01L 41/00* (2006.01)

(52) U.S. Cl. ...................... 600/459; 600/447; 310/318; 310/314

(58) Field of Classification Search ................ 600/459, 600/467, 444, 445, 447; 310/335, 314, 318
See application file for complete search history.

(56) References Cited

U.S. PATENT DOCUMENTS

| 4,374,525 | A | * | 2/1983 | Baba ........................... 600/463 |
| 4,448,075 | A | * | 5/1984 | Takemura et al. ............. 73/626 |
| 4,841,977 | A |   | 6/1989 | Griffith et al. |
| 5,081,993 | A | * | 1/1992 | Kitney et al. ................ 600/455 |
| 5,349,960 | A | * | 9/1994 | Gondo ....................... 600/455 |
| 5,630,873 | A |   | 5/1997 | Weiser et al. |
| 5,667,373 | A | * | 9/1997 | Wright et al. ............... 600/443 |
| 5,685,311 | A |   | 11/1997 | Hara et al. |
| 5,797,846 | A | * | 8/1998 | Seyed-Bolorforosh et al. ........................ 600/447 |

(Continued)

FOREIGN PATENT DOCUMENTS

JP        02-134142 A     5/1990

OTHER PUBLICATIONS

Schwarz, H. P. et al Institute of Electrical and Electronics Engineers: "A 100- Element Ultrasonic Circular Array for Endoscopic Application in Medicine and NDT" Proceedings of the Annual Conference of the Engineering in Medicine and Biology Society. Philadelphia, Nov. 1-4, 1990, New York, IEEE., US., vol. vol. 1 Conf. 12, Nov. 1, 1990, pp. 287-290, XP000239520.

(Continued)

*Primary Examiner*—Eric F Winakur
*Assistant Examiner*—Helene Bor
(74) *Attorney, Agent, or Firm*—Sughrue Mion, PLLC (57) ABSTRACT

In an ultrasonic endoscope capable of being inserted into a body of a patient and imaging ultrasonic tomographic images, a frame rate in electronic radial scanning operation is improved. The ultrasonic endoscope includes: an ultrasonic transducer unit including plural ultrasonic transducers, each having a first electrode and a second electrode, for transmitting and receiving ultrasonic waves; a plurality of first interconnections each connected to the first electrodes of predetermined ultrasonic transducers; and a plurality of second interconnections each connected to the second electrodes of ultrasonic transducers having the first electrodes not connected to each other; wherein the ultrasonic transducer unit performs scanning operation by simultaneously transmitting the same number of ultrasonic beams in each of plural angle regions when selectively supplied with drive signals via the plurality of first interconnections and the plurality of second interconnections.

14 Claims, 9 Drawing Sheets

U.S. PATENT DOCUMENTS

| | | | |
|---|---|---|---|
| 5,938,612 A * | 8/1999 | Kline-Schoder et al. | 600/459 |
| 6,171,248 B1 * | 1/2001 | Hossack et al. | 600/459 |
| 6,283,920 B1 * | 9/2001 | Eberle et al. | 600/459 |
| 6,468,221 B2 * | 10/2002 | Ohara et al. | 600/462 |
| 6,471,654 B2 * | 10/2002 | Ohara et al. | 600/463 |
| 6,776,763 B2 * | 8/2004 | Nix et al. | 600/466 |
| 6,780,157 B2 * | 8/2004 | Stephens et al. | 600/466 |
| 6,831,943 B1 * | 12/2004 | Dabak et al. | 375/147 |
| 6,873,868 B2 * | 3/2005 | Furnish | 600/435 |
| 6,899,682 B2 * | 5/2005 | Eberle et al. | 600/459 |
| 6,962,567 B2 * | 11/2005 | Eberle et al. | 600/466 |
| 2003/0181813 A1 * | 9/2003 | Ogawa | 600/443 |
| 2003/0213305 A1 | 11/2003 | Mamayek | |
| 2005/0085730 A1 * | 4/2005 | Flesch et al. | 600/459 |
| 2007/0165699 A1 * | 7/2007 | Dabak et al. | 375/146 |

OTHER PUBLICATIONS

Takeda, et al., The Experience of Electric Radial Endoscopic Ultrasonography on Gastroenterology, Jpn J Med Ultrasonics Supplement, 2004, p. 238, vol. 31, Japan.

\* cited by examiner

| COMBINATION No. | 1 | 2 | 3 | 4 | 5 | 6 |
|---|---|---|---|---|---|---|
| SENSITIVITY | s | 5s/4 | 6s/4 | 7s/4 | 8s/4 | 9s/4 |
| FRAME RATE | f | 4f/5 | 4f/6 | 4f/7 | 4f/8 | 4f/9 |
| COMBINATION No. | 7 | 8 | 9 | 10 | 11 | 12 | 13 |
| SENSITIVITY | 10s/4 | 11s/4 | 12s/4 | 13s/4 | 14s/4 | 15s/4 | 16s/4 |
| FRAME RATE | 4f/10 | 4f/11 | 4f/12 | 4f/13 | 4f/14 | 4f/15 | 4f/16 |

ULTRASONIC ENDOSCOPE AND ULTRASONIC ENDOSCOPIC APPARATUS

BACKGROUND OF THE INVENTION

1. Field of the Invention

The present invention relates to an ultrasonic endoscope capable of being inserted into a body of a patient and imaging ultrasonic tomographic images for medical diagnoses and an ultrasonic endoscopic apparatus including such an endoscope.

2. Description of a Related Art

Recent years, an ultrasonic endoscope has been used for medical diagnoses by inserting it into a body of a patient and imaging ultrasonic tomographic images. In such an ultrasonic endoscope, generally, a mechanical radial scanning method of performing scanning with viewing angle of 360° by mechanically rotating an array including plural ultrasonic transducers (ultrasonic vibrators) that transmit and receive ultrasonic waves has been adopted.

However, according to the mechanical radial scanning method, compared to a scanning method of performing scanning with viewing angle of 90° using a convex ultrasonic transducer array in an external ultrasonic imaging apparatus, in the case where conditions of sound ray density, scanning depth, etc. are set into the same condition, there is a problem that scanning time (frame period) for obtaining an image for one frame becomes longer in order to perform scanning with wide viewing angle and the frame rate becomes low.

On the other hand, an electronic radial scanning method of performing scanning with viewing angle of 360° by electronic scanning has been proposed. For example, Kinichi Takeda et al., "The Experience of Electric Radial Endoscopic Ultrasonography on Gastroenterology", Jpn J Med Ultrasonics, Vol. 31, Supplement (2004), 77-C062, pp. 238 discloses results from studies on efficacy and problems of an electronic radial ultrasonic endoscope based on experiences of using the electronic radial ultrasonic endoscope for various digestive system diseases.

Further, Japanese Patent Application Publication JP-A-2-134142 discloses an electronic radial ultrasonic beam apparatus having improved resolving power in which a flexible substrate on which plural ultrasonic vibrators are provided in a line is formed in a cylindrical shape and an interval between ultrasonic vibrators in the joint part of the flexible substrate is set to an integral multiple of an arrangement interval of the respective vibrators. Further, the apparatus includes drive element switching circuits and delay lines for enabling scanning operation at an interval position between the ultrasonic vibrators in the joint part by driving ultrasonic vibrators adjacent to the interval position (page 2, right upper column, line 14 to left lower column, line 3; page 4, right lower column, lines 2-10; and FIG. 3).

Figure 11A:
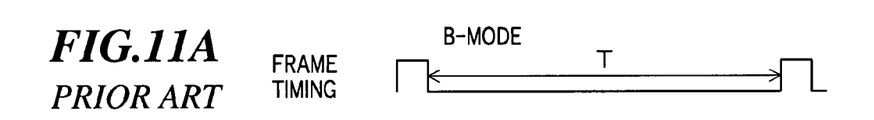
FIGS. 11A to 11D are charts for explanation of frame rates in a conventional ultrasonic endoscope.
Figure 11B:
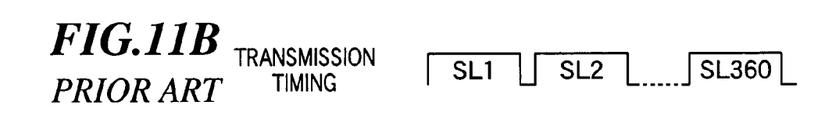

However, in the ultrasonic endoscope according to the electronic radial scanning method, in order to obtain a B-mode ultrasonic tomographic image with viewing angle of 360°, it is also required to sequentially transmit ultrasonic beams (sound rays) SL1 to SL360 in a frame period T as shown in FIG. 11A while varying the positions of ultrasonic transducers to be used along a circumferential direction as shown in FIG. 11B. Accordingly, compared to the case of performing scanning operation with viewing angle of 90° using a convex ultrasonic transducer array, the frame period T becomes about four times and the frame rate is reduced to about one-quarter.

Figure 11C:
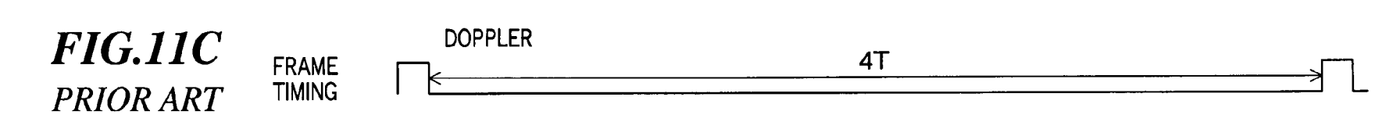
Figure 11D:
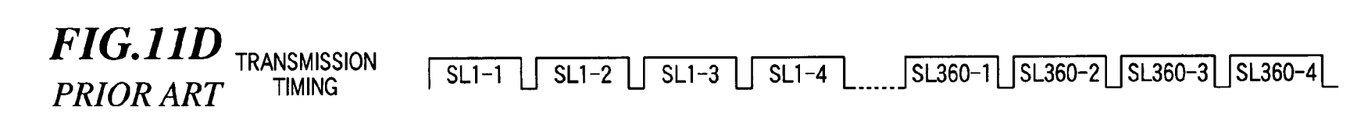

Further, in the electronic radial ultrasonic endoscope, in the case where bloodstream information is obtained by the Doppler method, in order to improve the S/N ratio of minute bloodstream information, plural pulses are sequentially transmitted in the same direction. For example, as shown in FIG. 11D, four ultrasonic beams SL1-1 to SL1-4 are sequentially transmitted in the first direction, and the transmission is repeated while varying the transmission direction, and finally, four ultrasonic beams SL360-1 to SL360-4 are sequentially transmitted in the 360th direction. In this case, compared to the case of imaging the B-mode tomographic image as shown in FIGS. 11A and 11B, the frame period T becomes about four times (4T) and the frame rate is reduced to about one-quarter as shown in FIG. 11C.

SUMMARY OF THE INVENTION

The present invention is achieved in view of the above-mentioned problems. An object of the present invention is to improve a frame rate in electronic radial scanning operation in an ultrasonic endoscope capable of being inserted into a body of a patient and imaging ultrasonic tomographic images.

In order to solve the above-mentioned problems, an ultrasonic endoscope according to one aspect of the present invention comprises: an ultrasonic transducer unit including plural ultrasonic transducers, each having a first electrode and a second electrode, for transmitting and receiving ultrasonic waves; a plurality of first interconnections each connected to the first electrodes of respective ones of the plural ultrasonic transducers; and a plurality of second interconnections each connected to the second electrodes of respective ones of the plural ultrasonic transducers having the first electrodes not connected to each other; wherein the ultrasonic transducer unit performs scanning operation by simultaneously transmitting the same number of ultrasonic beams in each of plural angle regions formed by dividing a scanning angle region by a predetermined angle when selectively supplied with drive signals via the plurality of first interconnections and the plurality of second interconnections.

Further, an ultrasonic endoscopic apparatus according to a first aspect of the present invention comprises: an ultrasonic endoscope having an ultrasonic transducer unit including plural ultrasonic transducers, each having a first electrode and a second electrode, for transmitting and receiving ultrasonic waves; and an ultrasonic observation apparatus for selectively supplying drive signals to the ultrasonic transducer unit such that the ultrasonic transducer unit performs scanning operation by simultaneously transmitting the same number of ultrasonic beams in each of plural angle regions formed by dividing a scanning angle region by a predetermined angle.

Furthermore, an ultrasonic endoscopic apparatus according to a second aspect of the present invention comprises: an ultrasonic endoscope having an ultrasonic transducer unit including plural ultrasonic transducers, each having a first electrode and a second electrode, for transmitting and receiving ultrasonic waves, a plurality of first interconnections each connected to the first electrodes of respective ones of the plural ultrasonic transducers, and a plurality of second interconnections each connected to the second electrodes of respective one of the plural ultrasonic transducers having the first electrodes not connected to each other; transmitting means for generating drive signals and supplying the drive signals to the ultrasonic transducer unit via the plurality of first interconnections; plural pieces of switch means connected to the plurality of second interconnections and a fixed potential; and control means for controlling the transmitting means such that scanning operation is performed by simultaneously transmitting the same number of ultrasonic beams in each of plural angle regions formed by dividing a scanning angle region by a predetermined angle and supplying control signals for controlling whether each of the plurality of second interconnections is connected to the fixed potential or not to the plural pieces of switch means.

According to the present invention, the frame rate can be improved by simultaneously transmitting the same number of ultrasonic beams at a certain angle interval in each of plural angle regions formed by dividing a scanning angle region by a predetermined angle. Further, in the case where the angle interval of the simultaneously transmitted ultrasonic beams is set to 90°, an influence of crosstalk between plural ultrasonic beams is reduced and image quality of ultrasonic tomographic images can be uniformized. Furthermore, the number of interconnections between the ultrasonic transducer unit and the main body (ultrasonic observation apparatus) is reduced, and thereby, the ultrasonic endoscope can be downsized while the cost is reduced.

DESCRIPTION OF THE PREFERRED EMBODIMENTS

Hereinafter, preferred embodiments of the present invention will be described in detail by referring to the drawings. The same reference numbers will be assigned to the same component elements and the description thereof will be omitted.

Figure 1:
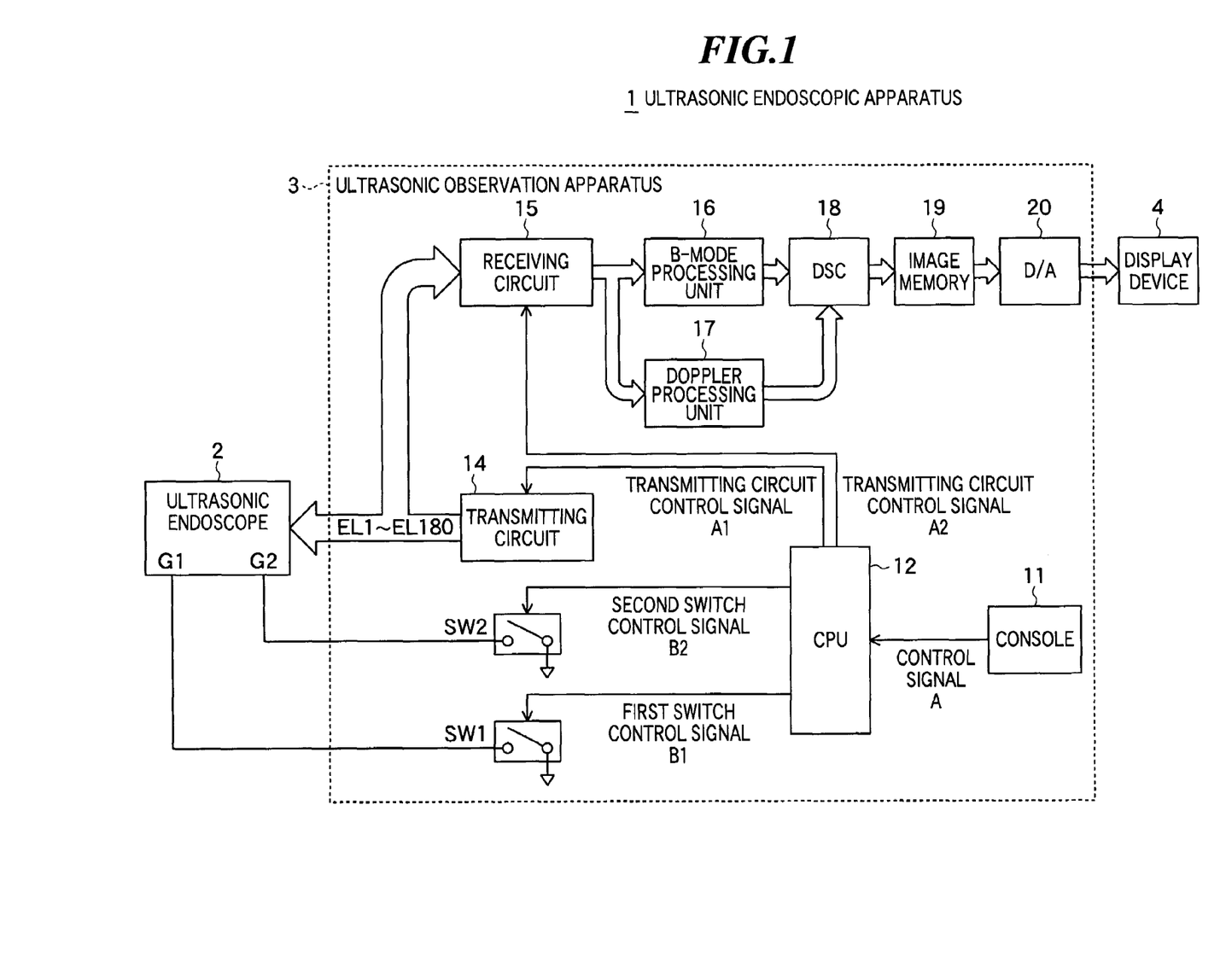
FIG. 1 is a block diagram showing a constitution of an ultrasonic endoscope apparatus 1 according to one embodiment of the present invention.

As shown in FIG. 1, an ultrasonic endoscope apparatus 1 according to one embodiment of the present invention includes an electronic radial ultrasonic endoscope 2, an ultrasonic observation apparatus 3 to which the ultrasonic endoscope 2 is connectable, a display device 4 connected to the ultrasonic observation apparatus 3.

The ultrasonic observation apparatus 3 includes a console 11, a CPU (central processing unit) 12, first and second switches SW1 and SW2, a transmitting circuit 14, a receiving circuit 15, a B-mode processing unit 16, a Doppler processing unit 17, a digital scan converter (DSC) 18, an image memory 19, and a digital/analog converter (D/A converter) 20.

Figure 2:
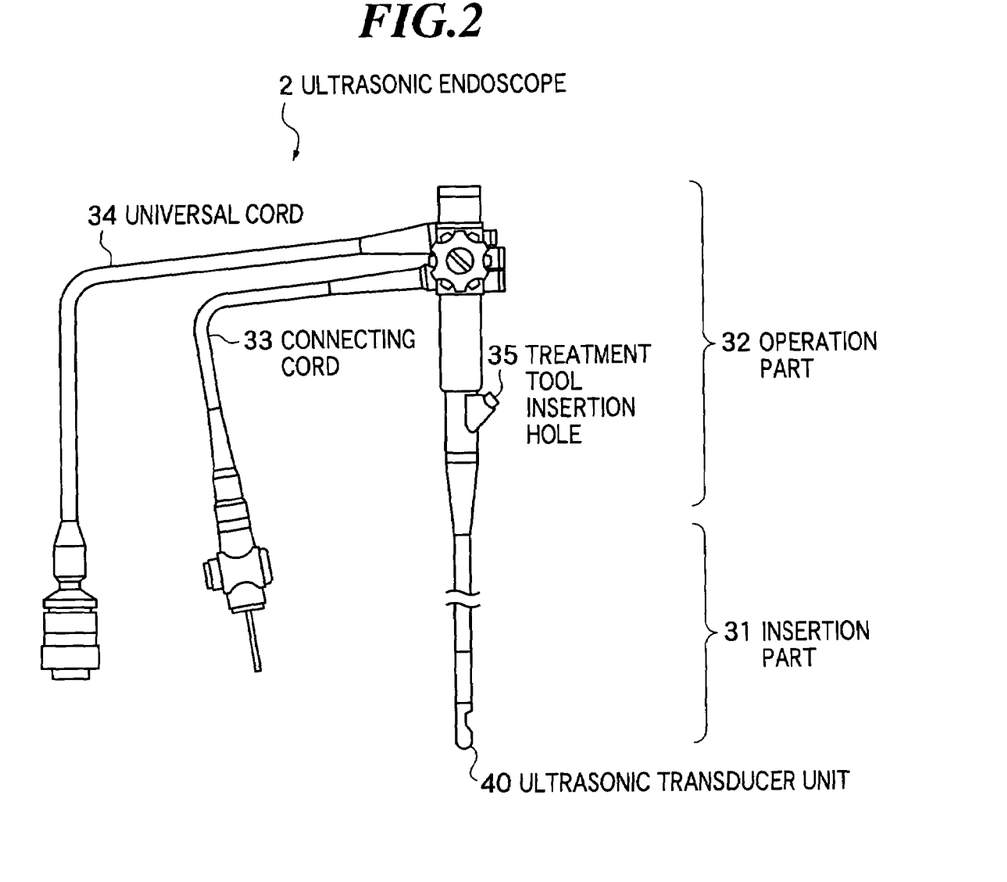
FIG. 2 shows a structure of an ultrasonic endoscope 2 shown in FIG. 1.

As shown in FIG. 2, the ultrasonic endoscope 2 includes an insertion part 31, an operation part 32, a connecting cord 33, and a universal cord 34.

The insertion part 31 of the ultrasonic endoscope 2 has an elongated flexible tubular shape so as to be inserted into a body of a patient. The operation part 32 is provided at the base end of the insertion part 31, connected to the ultrasonic observation apparatus 3 via the connecting cord 33 and connected to a light source device (not shown) via the universal cord 34.

In the insertion part 31 of the ultrasonic endoscope 2, an illumination window and an observation window are provided. An illumination lens for outputting illumination light supplied via a light guide from the light source device is attached to the illumination window. These form an illumination optical system. Further, an objective lens is attached to the observation window, and, in a position where the objective lens forms an image, an input end of an image guide or solid-state image sensor such as a CCD camera is disposed. These form an observation optical system.

Figure 3:
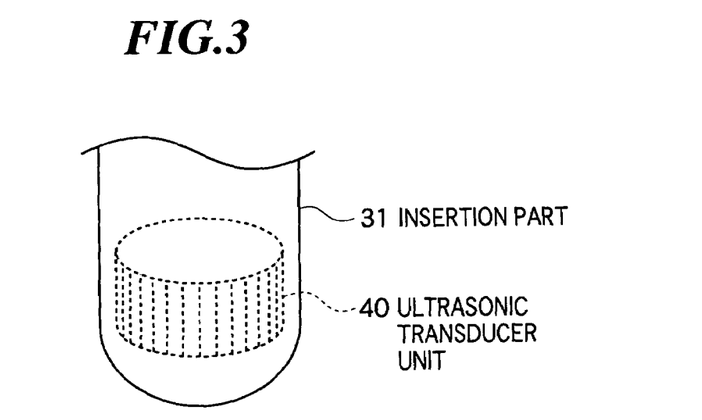
FIG. 3 is an enlarged view showing a tip of the ultrasonic endoscope 2 shown in FIG. 2.

FIG. 3 is an enlarged view showing the tip of the ultrasonic endoscope 2 shown in FIG. 2. At the tip of the insertion part 31 of the ultrasonic endoscope 2, an ultrasonic transducer unit 40 in which plural ultrasonic transducers are arranged on the circumference thereof. The ultrasonic transducer unit 40 transmits an ultrasonic beam according to drive signals supplied from the transmitting circuit 14 of the ultrasonic observation apparatus 3, receives ultrasonic echoes reflected from a target part or the like, and outputs plural reception signals to the receiving circuit 15 of the ultrasonic observation apparatus 3. Further, at the tip of the insertion part 31 of the ultrasonic endoscope 2, a hole is formed from which a treatment tool or the like inserted from a treatment tool insertion hole 35 provided in the operation part 32 is protruded.

Figure 4:
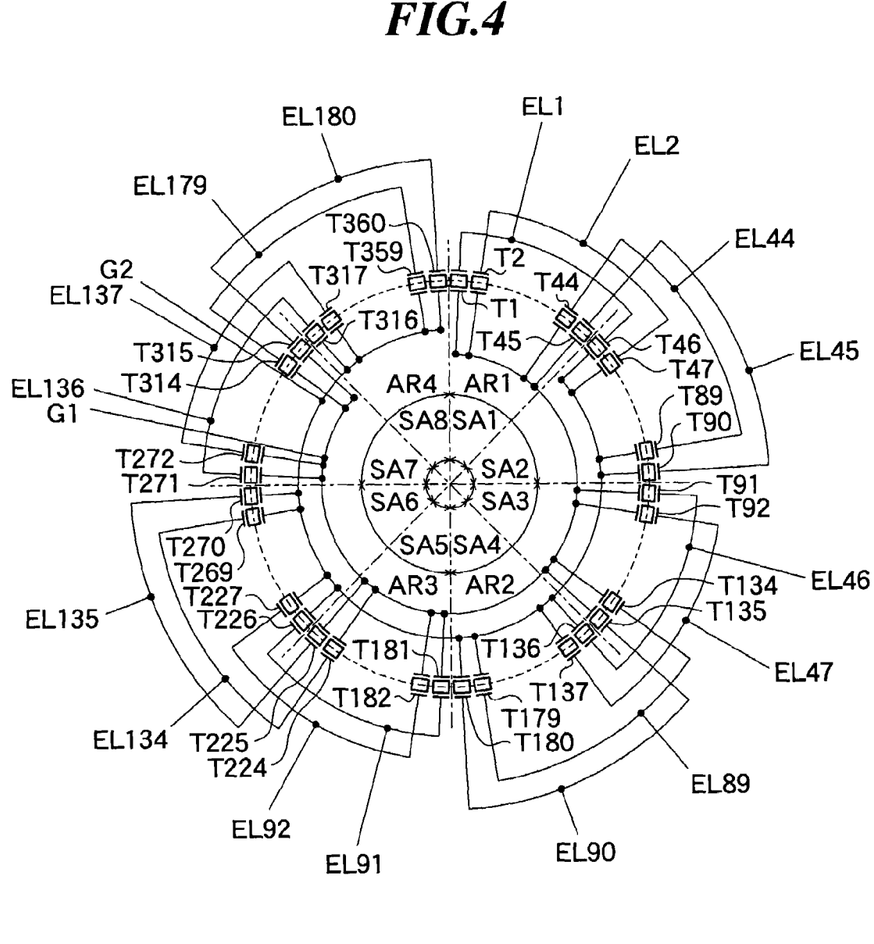
FIG. 4 shows a constitution of an ultrasonic transducer unit 40 shown in FIG. 2.

As shown in FIG. 4, the ultrasonic transducer unit 40 is formed by arranging 360 ultrasonic transducers T1 to T360 on the circumference thereof. Here, the ultrasonic transducers T1 to T360 are grouped as below, in order to divide a scanning angle region with viewing angle of 360° into four divisional regions (first to fourth divisional regions AR1 to AR4) by 90°, perform radial scanning by transmitting four ultrasonic beams with the same timing in the first to fourth divisional regions AR1 to AR4, respectively, and holding the intervals of the four ultrasonic beams transmitted with the same timing at 90°.

The first group of ultrasonic transducers consists of 45 ultrasonic transducers T1 to T45 that belong to a first sub region SA1 of two sub regions (first and second sub regions SA1 and SA2) formed by dividing the first divisional region AR1 shown in FIG. 4 by 45°. Accordingly, the range of scanning by the ultrasonic transducers T1 to T45 in the first group corresponds to the range of the first sub region SA1.

The second group of ultrasonic transducers consists of 45 ultrasonic transducers T46 to T90 that belong to the above-mentioned second sub region SA2. Accordingly, the range of scanning by the ultrasonic transducers T46 to T90 in the second group corresponds to the range of the second sub region SA2.

The third group of ultrasonic transducers consists of 45 ultrasonic transducers T91 to T135 that belong to a third sub region SA3 of two sub regions (third and fourth sub regions SA3 and SA4) formed by dividing the second divisional region AR2 shown in FIG. 4 by 45°. Accordingly, the range of scanning by the ultrasonic transducers T91 to T135 in the third group corresponds to the range of the third sub region SA3.

The fourth group of ultrasonic transducers consists of 45 ultrasonic transducers T136 to T180 that belong to the above-mentioned fourth sub region SA4. Accordingly, the range of scanning by the ultrasonic transducers T136 to T180 in the fourth group corresponds to the range of the fourth sub region SA4.

The fifth group of ultrasonic transducers consists of 45 ultrasonic transducers T181 to T225 that belong to a fifth sub region SA5 of two sub regions (fifth and sixth sub regions SA5 and SA6) formed by dividing the third divisional region AR3 shown in FIG. 4 by 45°. Accordingly, the range of scanning by the ultrasonic transducers T181 to T225 in the fifth group corresponds to the range of the fifth sub region SA5.

The sixth group of ultrasonic transducers consists of 45 ultrasonic transducers T226 to T270 that belong to the above-mentioned sixth sub region SA6. Accordingly, the range of scanning by the ultrasonic transducers T226 to T270 in the sixth group corresponds to the range of the sixth sub region SA6.

The seventh group of ultrasonic transducers consists of 45 ultrasonic transducers T271 to T315 that belong to a seventh sub region SA7 of two sub regions (seventh and eighth sub regions SA7 and SA8) formed by dividing the fourth divisional region AR4 shown in FIG. 4 by 45°. Accordingly, the range of scanning by the ultrasonic transducers T271 to T315 in the seventh group corresponds to the range of the seventh sub region SA7.

The eighth group of ultrasonic transducers consists of 45 ultrasonic transducers T316 to T360 that belong to the above-mentioned eighth sub region SA8. Accordingly, the range of scanning by the ultrasonic transducers T316 to T360 in the eighth group corresponds to the range of the eighth sub region SA8.

Each of the ultrasonic transducers T1 to T360 includes an ultrasonic vibrator formed by sandwiching a piezoelectric element of PZT, PVDF, or the like between an individual electrode and a common electrode. When a drive signal is applied to the individual electrode while the common electrode is connected to a fixed potential (for example, ground potential in the embodiment), the transducer transmits ultrasonic waves, and receives ultrasonic echoes reflected from a target part or the like and generates a reception signal in the individual electrode.

As shown in FIG. 4, in each of the first to fourth divisional regions AR1 to AR2, the individual electrodes of the two ultrasonic transducers located at 45° interval with respect to the circumferential direction of the ultrasonic transducer unit 40 are electrically connected to the same one of signal interconnections EL1 to EL 180.

For example, in the first divisional region AR1, the individual electrode of the ultrasonic transducer T1 within the first group and the individual electrode of the ultrasonic transducer T46 within the second group located at 45° interval with respect to the circumferential direction of the ultrasonic transducer unit 40 are electrically connected to the signal interconnection EL1. Similarly, the individual electrode of the ultrasonic transducer T2 within the first group and the individual electrode of the ultrasonic transducer T47 within the second group located at 45° interval with respect to the circumferential direction of the ultrasonic transducer unit 40 are electrically connected to the signal interconnection EL2.

Further, in the second divisional region AR2, the individual electrode of the ultrasonic transducer T91 within the third group and the individual electrode of the ultrasonic transducer T136 within the fourth group located at 45° interval with respect to the circumferential direction of the ultrasonic transducer unit 40 are electrically connected to the signal interconnection EL46. Similarly, the individual electrode of the ultrasonic transducer T92 within the third group and the individual electrode of the ultrasonic transducer T137 within the fourth group located at 45° interval with respect to the circumferential direction of the ultrasonic transducer unit 40 are electrically connected to the signal interconnection EL47.

On the other hand, the common electrodes of the ultrasonic transducers of the same group are electrically connected to the same one of the common electrode interconnections G1 and G2, and the common electrodes of the ultrasonic transducers of the plural groups located at each 90° interval with respect to the circumferential direction of the ultrasonic transducer unit 40 are also electrically connected to the same one of the common electrode interconnections G1 and G2.

That is, the common electrodes of the ultrasonic transducers T1 to T45, T91 to T135, T181 to T225, and T271 to T315 of the odd number (the first, third, fifth, and seventh) groups located at each 90° interval with respect to the circumferential direction of the ultrasonic transducer unit 40 are electrically connected to the common electrode interconnection G1. Further, the common electrodes of the ultrasonic transducers T46 to T90, T136 to T180, T226 to T270, and T316 to T380 of the even number (the second, fourth, sixth, and eighth) groups located at each 90° interval with respect to the circumferential direction of the ultrasonic transducer unit 40 are electrically connected to the common electrode interconnection G2.

Since the individual electrodes and the common electrodes of the ultrasonic transducers T1 to T360 are thus interconnected, and then, the number of interconnections becomes "182" as the sum of "180" as the number of signal interconnections EL1 to EL180, and "2" as the number of common electrode interconnections G1 and G2. Consequently, the number of interconnections can be reduced to the half of the number of interconnections "361"(=360+1) in the case where signal interconnections are provided to the individual electrodes of the ultrasonic transducers T1 to T360, respectively, and one common electrode interconnection is wired to the common electrodes.

The signal interconnections EL1 to EL180 are connected to the transmitting circuit 14 and the receiving circuit 15 of the ultrasonic observation apparatus 3 shown in FIG. 1 via the connecting cord 33 shown in FIG. 2, and the common electrode interconnections G1 and G2 are connected to the first and second switches SW1 and SW2 of the ultrasonic observation apparatus 3 via the connecting cord 23.

The console 11 of the ultrasonic observation apparatus 3 shown in FIG. 1 outputs control signal A for controlling start/stop of ultrasonic imaging operation in the ultrasonic endoscope 2 and mode selection (B-mode or Doppler mode, and frame rate priority mode or sensitivity priority mode) to the CPU 12 according to the operation of an operator.

The CPU 12 generates first and second switch control signals B1 and B2 for controlling ON/OFF of the first and second switches SW1 and SW2 based on the control signal A input from the console 11 and outputs those signals to the first and second switches SW1 and SW2, respectively. Further, the CPU 12 outputs transmitting circuit control signal A1 for controlling the operation of the transmitting circuit 14 to the transmitting circuit 14, and outputs receiving circuit control signal A2 for controlling the operation of the receiving circuit 15 to the receiving circuit 15.

The first and second switches SW1 and SW2 are turned ON/OFF according to the first and second switch control signals B1 and B2 input from the CPU 12. When the first and second switches SW1 and SW2 are turned ON, the common electrode interconnections G1 and G2 are grounded, respectively, and, when the first and second switches SW1 and SW2 are turned OFF, the common electrode interconnections G1 and G2 are opened, respectively. Since the ultrasonic transducer is operated only when the common electrode is grounded, the ultrasonic transducers T1 to T360 can be operated separately in the odd number (the first, third, fifth, and seventh) groups and the even number (the second, fourth, sixth, and eighth) groups.

The transmitting circuit 14 generates drive signals based on the transmitting circuit control signal A1, and outputs these drive signals to the signal interconnections EL1 to EL 180. According to these drive signals, ultrasonic waves are transmitted from the ultrasonic transducers of groups with the grounded common electrodes.

On the other hand, the receiving circuit 15 amplifies the reception signals input from the ultrasonic transducers of groups with the grounded common electrodes via the signal interconnections EL1 to EL 180 at a predetermined amplification degree, and then, converts the amplified reception signals into digital reception signals by performing A/D conversion. Further, the receiving circuit 15 performs reception focus processing by performing processing of phase matching or the like on the digital reception signals to form sound ray data in which focal points of the ultrasonic echoes are narrowed.

The B-mode processing unit 16 performs correction of attenuation depending on the distance according to the depth of the reflection position of ultrasonic waves on the sound ray data formed by the receiving circuit 15 and performs envelope detection processing thereon to generate B-mode image data.

The Doppler processing unit 17 removes high frequency components from the reception signals that have been subjected to the reception focus processing based on the sound ray data formed by the receiving circuit 15, and performs orthogonal phase detection processing on the reception signals. Further, the Doppler processing unit 17 removes unwanted clutter components caused by the variations in specular echoes of blood vessel wall, heart wall, or the like from the reception signals that have been subjected to orthogonal phase detection. Thus, Doppler image data formed by extracting only reflection components from bloodstream is generated.

Since the B-mode image data generated in the B-mode processing unit 16 and the Doppler image data generated in the Doppler processing unit 17 have been obtained by the scanning method different from the normal scanning method of television signal, the DSC 18 converts (raster conversion) the data into normal image data. The image memory 19 stores the image data generated in the DSC 18. The D/A converter 20 converts the digital image data read from the image memory 19 into analog image signals and outputs them to the display unit 4. Thereby, in the display unit 4, an ultrasonic tomographic image imaged by the ultrasonic endoscope 2 is displayed.

Next, an operation of the ultrasonic endoscopic apparatus 1 according to the embodiment will be described.

In the case where an ultrasonic tomographic image is imaged using the ultrasonic endoscope 2 shown in FIG. 2, the operator emits light from the light source connected to one end of the universal cord 34 and outputs illumination light into the body of the patient from the illumination window provided at the tip of the insertion part 31, and inserts the insertion part 31 of the ultrasonic endoscope 2 into the body of the patient while observing the insertion state from the observation window.

First, the operation of the ultrasonic endoscopic apparatus in the case of imaging a B-mode image will be described. When the insertion part 31 reaches a target position, the operator allows the console 11 to output the control signal A for starting the operation of the ultrasonic endoscope 2 and designating B-mode to the CPU 12 by operating the console 11 (FIG. 1).

The CPU 12 outputs the transmitting circuit control signal A1 for instructing start of the operation of the transmitting circuit 14 and generation of the drive signals for B-mode to the transmitting circuit 14. Further, the CPU 12 outputs the receiving circuit control signal A2 for instructing start of the operation of the receiving circuit 15 to the receiving circuit 15.

Furthermore, the CPU 12 outputs the first switch control signal B1 for turning ON the first switch SW1 to the first switch SW1. When the first switch SW1 is turned ON, the common electrode interconnection G1 is grounded and the common electrodes of the ultrasonic transducers T1 to T45, T91 to T135, T181 to T225, and T271 to T315 of the odd number (the first, third, fifth, and seventh) groups shown in FIG. 4 are grounded.

The transmitting circuit 14 generates drive signals (pulse signals in the embodiment) to be respectively supplied to the individual electrodes of the ultrasonic transducers T1 to T45, T91 to T135, T181 to T225, and T271 to T315 of the odd number (the first, third, fifth, and seventh) groups via the signal interconnections EL1 to EL180. Simultaneously, the transmitting circuit 14 generates those drive signals such that four ultrasonic beams are transmitted from points separated at 90° from each other using three ultrasonic transducers for forming each one ultrasonic beam.

Figures 5A, 5B:
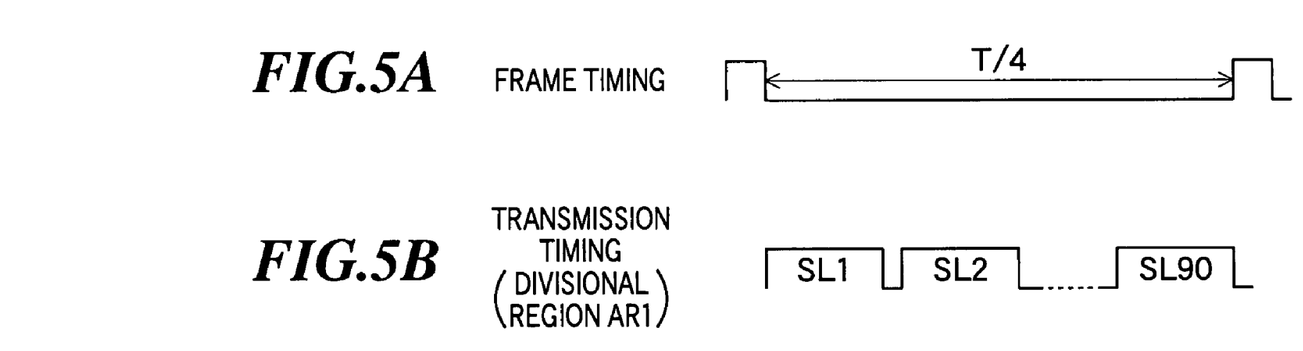
FIGS. 5A to 5E are charts for explanation of a frame rate when the ultrasonic endoscope 2 shown in FIG. 1 is driven in B-mode.
Figure 5C:
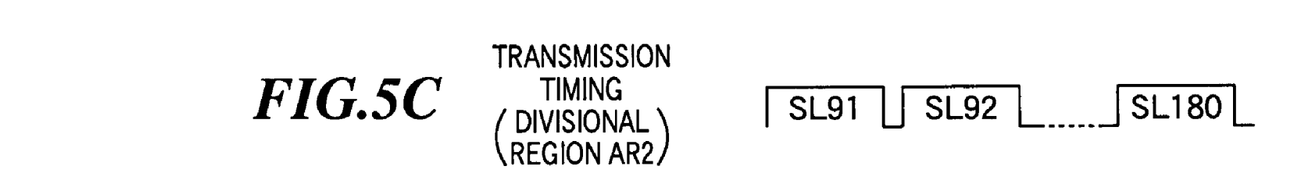
Figure 5D:
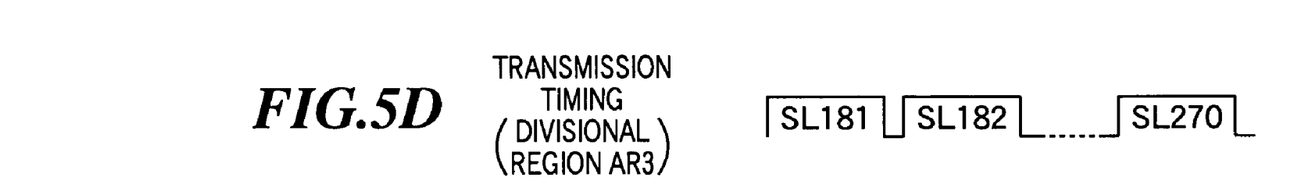
Figure 5E:
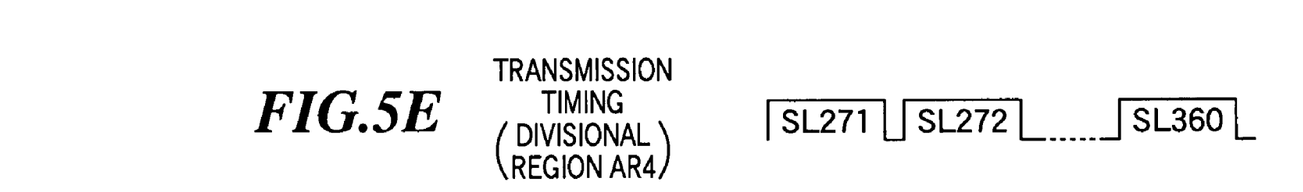

For example, when scanning for one frame is started as shown in FIG. 5A, first, drive pulse signals for driving the ultrasonic transducers are generated as shown in FIGS. 5B to 5E such that the ultrasonic beam (sound ray) SL1 (FIG. 5B) is transmitted from the ultrasonic transducers T1 to T3 within the first group in the divisional region AR1, the ultrasonic beam SL91 (FIG. 5C) is transmitted from the ultrasonic transducers T91 to T93 within the third group in the divisional region AR2, the ultrasonic beam SL181 (FIG. 5D) is transmitted from the ultrasonic transducers T181 to T183 within the fifth group in the divisional region AR3, and the ultrasonic beam SL271 (FIG. 5E) is transmitted from the ultrasonic transducers T271 to T273 within the seventh group in the divisional region AR4.

The plural reception signals obtained by receiving ultrasonic echoes generated by the reflection of these ultrasonic beams from the object are output to the receiving circuit 15 via the signal interconnections EL1 to EL 180 and sound ray data is formed and B-mode image data is generated in the B-mode processing unit 16, and then, the data is raster-converted in the DSC 18 and image data is formed. The image data is stored in the image memory 19.

When the scanning by the ultrasonic transducers T1 to T45, T91 to T135, T181 to T225, and T271 to T315 of the odd number (the first, third, fifth, and seventh) groups is finished, the CPU 12 outputs the first switch control signal B1 for turning OFF the first switch SW1 to the first switch SW1 and outputs the second switch control signal B2 for turning ON the second switch SW2 to the second switch SW2. Thereby, the common electrode interconnection G2 is grounded and the common electrodes of the ultrasonic transducers T46 to T90, T136 to T180, T226 to T270, and T316 to T380 of the even number (the second, fourth, sixth, and eighth) groups are grounded.

The transmitting circuit 14 generates plural drive pulse signals to be supplied to the individual electrodes of the ultrasonic transducers T46 to T90, T136 to T180, T226 to T270, and T316 to T380 of the even number (the second, fourth, sixth, and eighth) groups via the signal interconnections EL1 to EL 180, respectively, as is the case for the ultrasonic transducers of the odd number groups.

The plural reception signals obtained by receiving ultrasonic echoes generated by the reflection of these ultrasonic beams from the object are output to the receiving circuit 15 via the signal interconnections EL1 to EL 180 and sound ray data is formed and B-mode image data is generated in the B-mode processing unit 16, and then, the data is raster-converted in the DSC 18 and image data is formed. The image data is stored in the image memory 19.

Thus, by alternately driving the ultrasonic transducers of the odd number and even number groups and convex-scanning the respective divisional regions, the scanning angle range of total 360° of viewing angle is radially scanned. By the way, the scanning angle range is not limited to 360° but may be set to 180° or other values. The image data read from the image memory 19 is converted into analog image signals by the D/A converter 20 and output to the display device 4. Thereby, a B-mode ultrasonic tomographic image is displayed on the display device 4.

By the ultrasonic endoscopic apparatus according to the embodiment, since the ultrasonic beams are transmitted in four directions with the same timing, in the B-mode, compared to the frame period T shown in FIG. 11A in the conventional case where the ultrasonic beam is transmitted one by one, the frame period can be reduced to one-quarter (e.g., T/4) as shown in FIG. 5A and the frame rate can be increased to four times. Further, since the angular interval between the four ultrasonic beams transmitted with the same timing is 90°, the crosstalk due to simultaneous transmission of plural ultrasonic beams may hardly occur.

However, since the ultrasonic transducers in the adjacent sub regions can not be used for transmitting ultrasonic beams near the boundaries of the sub regions SA1 to SA8 (e.g., around the time of switching of groups of ultrasonic transducers by the first and second switches SW1 and SW2), irregularities in ultrasonic beams are caused.

Figure 8:
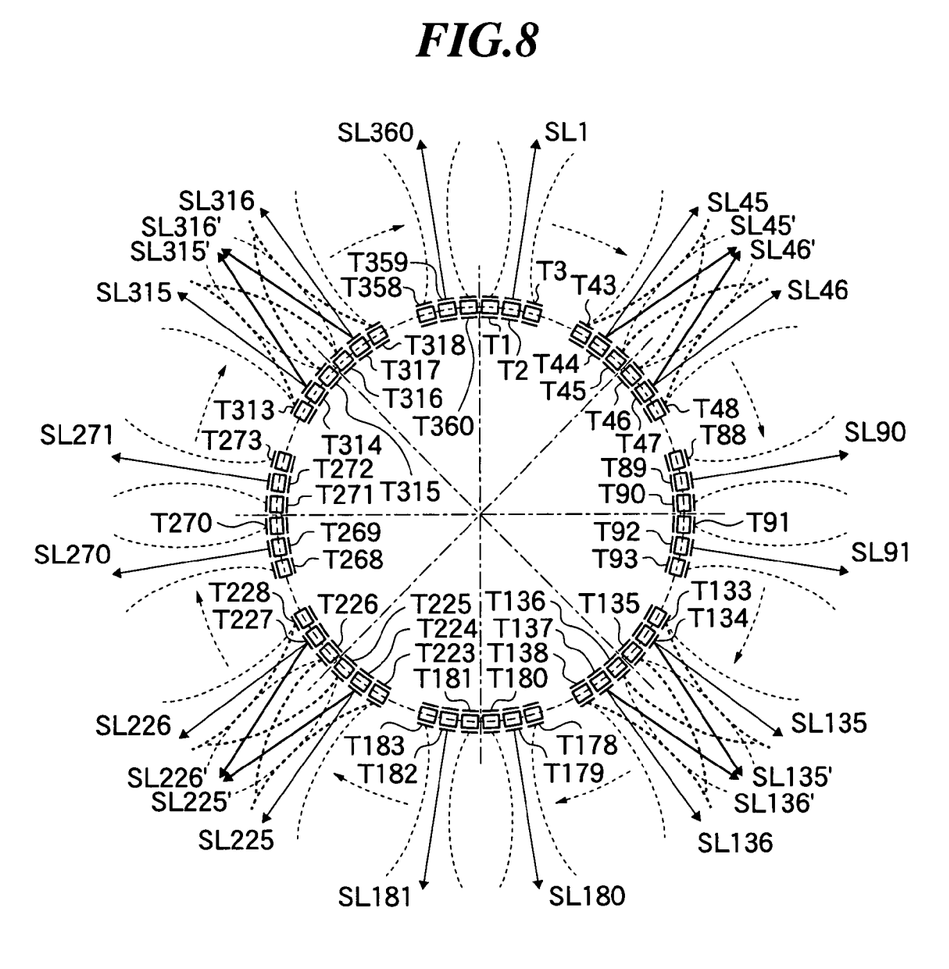
FIG. 8 is a diagram for explanation of steering operation at boundaries between sub regions.

Accordingly, for example, after the ultrasonic beam SL45 is transmitted, by controlling the delay amounts of the drive pulse signals to be supplied to the individual electrodes of the ultrasonic transducers T43, T44, and T45 within the first group, which have been used for transmission of the ultrasonic beam SL45, so as to steer the ultrasonic beam (sector scan), the ultrasonic beam SL45' is transmitted toward the second sub region SA2 side than the ultrasonic beam SL45 as shown in FIG. 8.

Then, before the ultrasonic beam SL46 is transmitted using the ultrasonic transducers T46, T47, and T48 within the second group, by controlling the delay amounts of the drive pulse signals to be supplied to the individual electrodes of these ultrasonic transducers T46, T47, and T48 so as to steer the ultrasonic beam (sector scan), the ultrasonic beam SL46' is transmitted toward the first sub region SA1 side than the ultrasonic beam SL46 as shown in FIG. 8. Thereby, irregularities in the ultrasonic beams at the boundary between the first sub region SA1 and the second sub region SA2 can be reduced.

Further, also at the boundary between the third and fourth sub regions SA3 and SA4, at the boundary between the fifth and sixth sub regions SA5 and SA6, and, at the boundary between the seventh and eighth sub regions SA7 and SA8, when steering the ultrasonic beam SL45', by simultaneously steering the ultrasonic beams SL135', SL225', SL315' (sector scan), and, when steering the ultrasonic beam SL46', by simultaneously steering the ultrasonic beams SL136', SL226', SL316' (sector scan), the reduction in frame rate due to increase in the number of ultrasonic beams is prevented.

Next, an operation of the ultrasonic endoscopic apparatus in the case where a Doppler mode image is imaged with frame rate priority will be described. The operator operates the console 11 (FIG. 1) to start the operation of the ultrasonic endoscope 2 and allows the console 11 to output the control signal A for instructing the Doppler mode with frame rate priority to the CPU 12.

The CPU 12 outputs the transmitting circuit control signal A1 for instructing start of the operation of the transmitting circuit 14 and generation of the drive signals for Doppler mode to the transmitting circuit 14. Further, the CPU 12 outputs the receiving circuit control signal A2 for instructing start of the operation of the receiving circuit 15 to the receiving circuit 15. In the Doppler mode with frame rate priority, the transmitting circuit 14 generates drive pulse signals such that four ultrasonic beams (pulses) are continuously transmitted at four times in four directions, respectively.

Figure 6A:
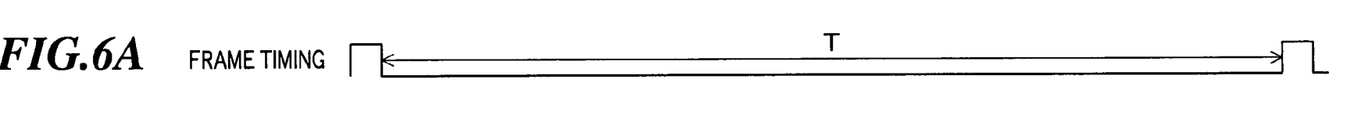
FIGS. 6A to 6E are charts for explanation of a frame rate when the ultrasonic endoscope 2 shown in FIG. 1 is driven in Doppler mode with frame rate priority.
Figure 6B:
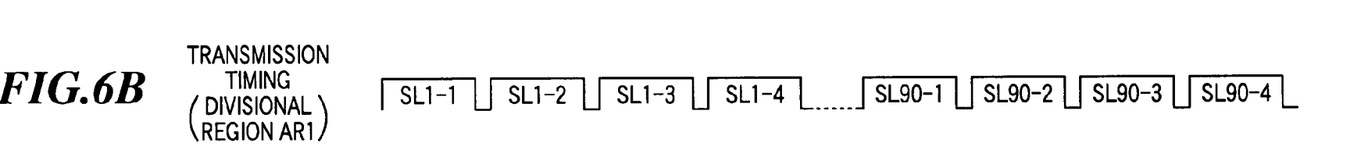
Figure 6C:
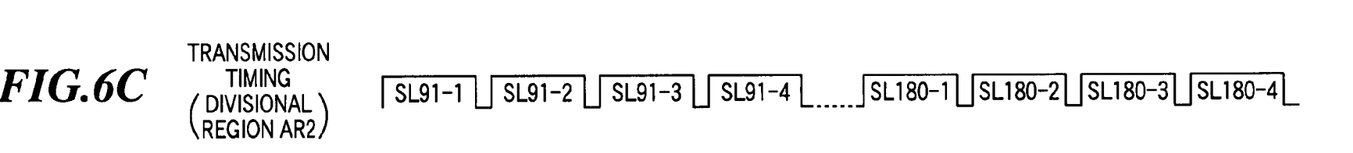
Figure 6D:
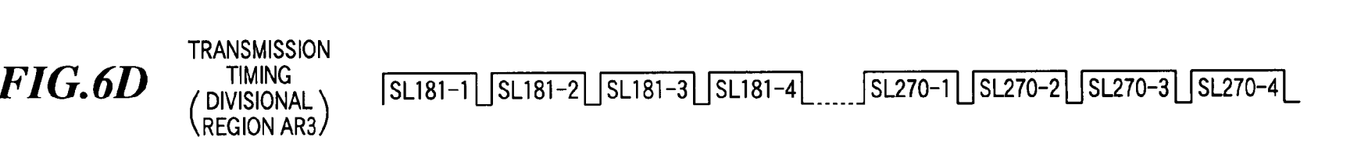
Figure 6E:
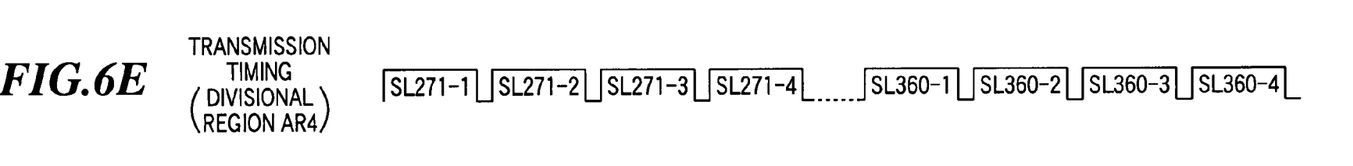

For example, when scanning for one frame is started as shown in FIG. 6A, first, drive pulse signals for driving the ultrasonic transducers are generated as shown in FIGS. 6B to 6E such that the continuous four ultrasonic beams (sound rays) SL1-1 to SL1-4 (FIG. 6B) are transmitted from the ultrasonic transducers T1 to T3 within the first group in the divisional region AR1, the continuous four ultrasonic beams SL91-1 to SL91-4 (FIG. 6C) are transmitted from the ultrasonic transducers T91 to T93 within the third group in the divisional region AR2, the continuous four ultrasonic beams SL181-1 to SL181-4 (FIG. 6D) are transmitted from the ultrasonic transducers T181 to T183 within the fifth group in the divisional region AR3, and the continuous four ultrasonic beams SL271-1 to SL271-4 (FIG. 6E) are transmitted from the ultrasonic transducers T271 to T273 within the seventh group in the divisional region AR4.

The plural reception signals obtained by receiving ultrasonic echoes generated by the reflection of these ultrasonic beams from the object are output to the receiving circuit 15 via the signal interconnections EL1 to EL180 and sound ray data is formed and Doppler mode image data is generated in the Doppler mode processing unit 17, and then, the data is raster-converted in the DSC 18 and image data is formed. The image data is stored in the image memory 19.

Thus, by convex-scanning the respective divisional regions, the entire scanning angle range is radial-scanned. Furthermore, as well as in the first embodiment, the ultrasonic beam is steered (sector scan) near the boundaries of the sub regions SA1 to SA8. Further, the image data stored in the image memory 19 is read, converted into analog image signals by the D/A converter 20, and output to the display device 4. Thereby, a Doppler image with frame rate priority is displayed in the display device 4.

According to the Doppler mode with frame rate priority, since the operation that four ultrasonic beams are transmitted in four directions are repeated at four times, compared to the frame period 4T shown in FIG. 11B in the conventional case where one ultrasonic beam is transmitted continuously at four times, the frame period can be reduced to one-quarter (e.g., T) as shown in FIG. 6A and the frame rate can be increased to four times.

By the way, in the case where bloodstream information at the location where the pounding of the heart is heavy, the Doppler mode with frame rate priority in which the number of repeated times for repeatedly transmitting the ultrasonic beam in the same direction is reduced is preferable, while, in the case where bloodstream information at the location where the blood flow rate is small, the Doppler mode with sensitivity priority in which the number of repeated times for repeatedly transmitting the ultrasonic beam in the same direction is increased is preferable.

In the case where a Doppler image is imaged in the Doppler mode with sensitivity priority, the operator operates the console 11 (FIG. 1) to start the operation of the ultrasonic endoscope 2 and allows the console 11 to output the control signal A for instructing the Doppler mode with sensitivity priority to the CPU 12.

The CPU 12 outputs the transmitting circuit control signal A1 for instructing start of the operation of the transmitting circuit 14 and generation of the drive signals for Doppler mode with sensitivity priority to the transmitting circuit 14. Further, the CPU 12 outputs the receiving circuit control signal A2 for instructing start of the operation of the receiving circuit 15 to the receiving circuit 15. In the Doppler mode with sensitivity priority, the transmitting circuit 14 generates drive pulse signals such that four ultrasonic beams (pulses) are continuously transmitted at 16 times in four directions, respectively.

Figure 7A:
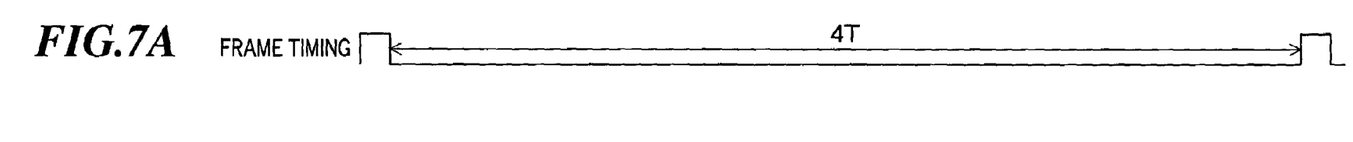
FIGS. 7A to 7E are charts for explanation of a frame rate when the ultrasonic endoscope 2 shown in FIG. 1 is driven in Doppler mode with sensitivity priority.
Figure 7B:
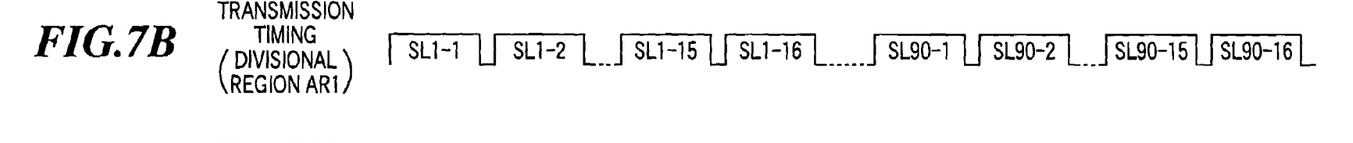
Figure 7C:
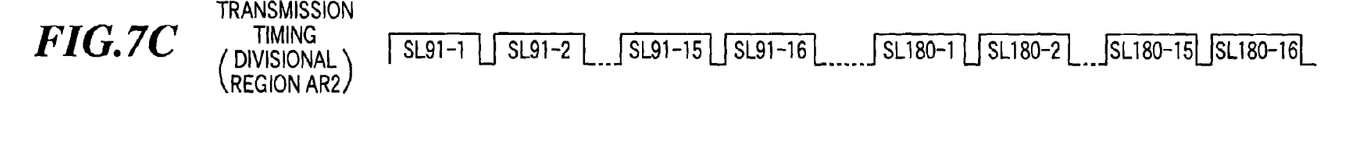
Figure 7D:
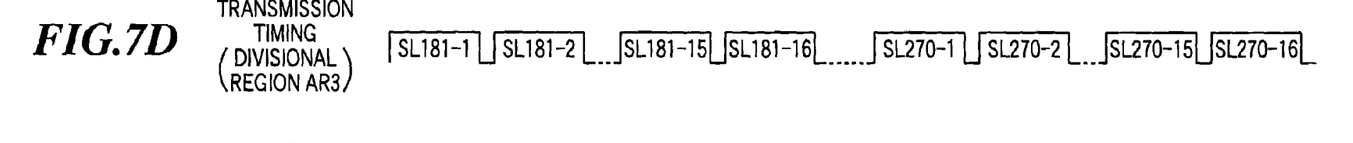
Figure 7E:
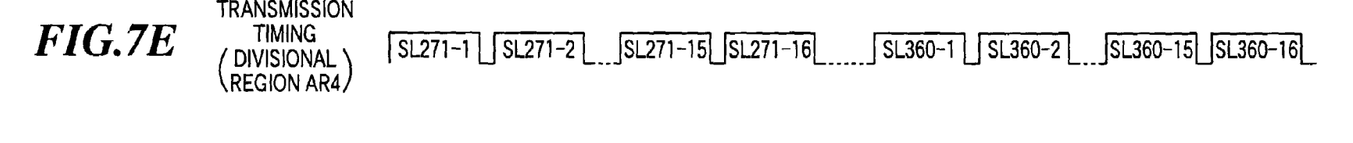

For example, when scanning for one frame is started as shown in FIG. 7A, first, drive pulse signals for driving the ultrasonic transducers are generated as shown in FIGS. 7B to 7E such that the continuous 16 ultrasonic beams (sound rays) SL1-1 to SL1-16 (FIG. 7B) are transmitted from the ultrasonic transducers T1 to T3 within the first group in the divisional region AR1, the continuous 16 ultrasonic beams SL91-1 to SL91-16 (FIG. 7C) are transmitted from the ultrasonic transducers T91 to T93 within the third group in the divisional region AR2, the continuous four ultrasonic beams SL181-1 to SL181-16 (FIG. 7D) are transmitted from the ultrasonic transducers T181 to T183 within the fifth group in the divisional region AR3, and the continuous four ultrasonic beams SL271-1 to SL271-16 (FIG. 7E) are transmitted from the ultrasonic transducers T271 to T273 within the seventh group in the divisional region AR4.

Then, by the same operation as in the above-mentioned Doppler mode with frame rate priority, a Doppler image with more improved sensitivity than in the case of frame rate priority is displayed in the display apparatus 4.

According to the Doppler mode with sensitivity priority, since the operation that four ultrasonic beams are transmitted in four directions are repeated at 16 times, compared to the frame period 16T in the conventional case where the operation that one ultrasonic beam is transmitted is repeated at 16 times, the frame period can be reduced to one-quarter (e.g., 4T) as shown in FIG. 7A and the frame rate can be increased to four times.

Figure 9:
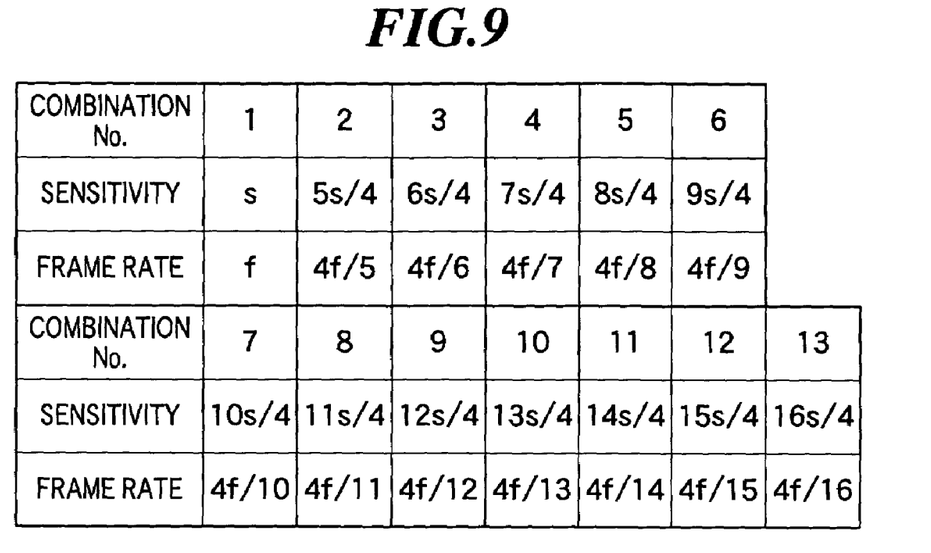
FIG. 9 shows an example of combination of frame rate and sensitivity.
Figure 10:
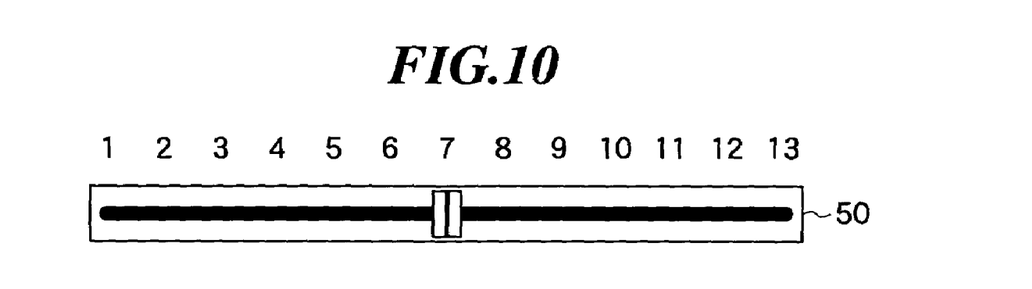
FIG. 10 shows a slide switch for selection of one of combinations of frame rate and sensitivity.

With respect to the frame rate priority and sensitivity priority in the Doppler mode, for example, a slide switch 50 as shown in FIG. 10 may be provided in the console 11 in FIG. 1 for the operator to select one of 14 combinations of sensitivity s and frame rate f (=1/T) as shown in FIG. 9. Thereby, the operator can finely select sensitivity s and frame rate f as usage and the user-friendliness is improved.

In the above-mentioned embodiments, radial scan has been performed while transmitting the ultrasonic beams with the same timing one by one in the first to fourth divisional regions AR1 to AR4, however, radial scan may be performed while transmitting the plural ultrasonic beams in the respective divisional regions.

Further, the scanning angle region of 360° has been divided into four divisional regions at each 90°, however, the angle at which the scanning angle region is divided may be not 90°. For example, the scanning angle region of 360° may be divided into two divisional regions at each 180°, and radial scan may be performed while transmitting a predetermined number of ultrasonic beams with the same timing in the respective divisional regions.

Furthermore, the respective first to fourth divisional regions AR1 to AR4 have been divided into sub regions SA1 to SA8 at each 45° and the ultrasonic transducers have been grouped with respect to each of the sub regions SA1 to SA8, however, the angle at which the respective divisional regions are divided into sub regions may be not 45°.

For example, the ultrasonic transducers may be grouped in 12 by dividing the respective first to fourth divisional regions AR1 to AR4 into sub regions SA1 to SA12 at each 30°. In this case, the number of signal interconnections is 120 and the individual electrodes of the three ultrasonic transducers separated at each 30° of the plural ultrasonic transducers are electrically connected to the same signal interconnection in the respective first to fourth divisional regions AR1 to AR4.

Further, in the case, the number of common electrode interconnections G is three, and the common electrodes of the ultrasonic transducers in the same group are electrically connected to the same common electrode interconnection, and the common electrodes of the ultrasonic transducers in the plural groups located at 90° intervals with respect to the circumferential direction of the ultrasonic transducer unit 40 are electrically connected to the same common electrode interconnection. Accordingly, three switches are provided in the ultrasonic observation apparatus 3 shown in FIG. 1, and one of the three switches is turned ON according to three switch control signals supplied from the CPU 12.

In the above embodiments, electronic radial ultrasonic endoscope has been described, however, the present invention can be applied to a convex ultrasonic endoscope in which 180 ultrasonic transducers are arranged in a semicircular form by dividing the region of 180° as a scanning full angle is divided into two divisional regions at each 90°, and performing scanning by transmitting ultrasonic beams one by one with the same timing in the respective divisional regions.

Further, the first and second switches SW1 and SW2 shown in FIG. 1 have been provided in the ultrasonic observation apparatus 3, however, they may be provided in the ultrasonic endoscope 2.

Furthermore, the control signal A for controlling the start/stop of the ultrasonic imaging operation in the ultrasonic endoscope 2 and indicating the mode has been output from the console 11, however, for example, a button for generating the control signal A may be provided in the operation part 32 of the ultrasonic endoscope 2 and the control signal A may be output from the operation part 32 to the CPU 12.

The invention claimed is:

1. An ultrasonic endoscope comprising:
   an ultrasonic transducer unit including plural ultrasonic transducers, each having a first electrode and a second electrode, for transmitting and receiving ultrasonic waves, said plural ultrasonic transducers being provided in plural angle regions formed by dividing a scanning angle region by predetermined angle, each of said plural angle region being divided into a first sub region and a second sub region;
   a plurality of first interconnections each connected to the first electrodes of a first respective one of said plural ultrasonic transducers provided in the first sub region and a second respective one of said plural ultrasonic transducers provided in the second sub region within a corresponding one of said plural angle regions; and a plurality of second interconnections each connected to the second electrodes of ultrasonic transducers provided in respective one of the first sub regions and the second sub regions;

wherein said ultrasonic transducer unit performs scanning operation by simultaneously transmitting a same number of ultrasonic beams in each of said plural angle regions when selectively supplied with drive signals via said plurality of first interconnections and said plurality of second interconnections.

2. An ultrasonic endoscope according to claim 1, wherein:
each of said plural angle regions is divided into the first and second sub regions by a second predetermined angle; and
each of said plurality of first interconnections is connected to the first electrodes of the first respective one and the second respective one of said plural ultrasonic transducers located at said second predetermined angle.

3. An ultrasonic endoscope according to claim 1, wherein:
said predetermined angle is 90°; and
said ultrasonic transducer unit performs scanning operation by simultaneously transmitting plural ultrasonic beams at an angle interval of 90° when selectively supplied with the drive signals via said plurality of first interconnections and said plurality of second interconnections.

4. An ultrasonic endoscopic apparatus comprising:
an ultrasonic endoscope having an ultrasonic transducer unit including plural ultrasonic transducers, each having a first electrode and a second electrode, for transmitting and receiving ultrasonic waves, said plural ultrasonic transducers being provided in plural angle regions formed by dividing a scanning angle region by a predetermined angle, each of said plural angle regions being divided into a first sub region and a second sub region, a plurality of first interconnections each connected to the first electrodes of a first respective one of said plural ultrasonic transducers provided in the first sub region and a second respective one of said plural ultrasonic transducers provided in the second sub region within corresponding one of said plural angle regions, and a plurality of second interconnections each connected to the second electrodes of ultrasonic transducers provided in respective one of the first sub regions and the second sub regions; and
an ultrasonic observation apparatus for selectively supplying drive signals to said ultrasonic transducer unit such that said ultrasonic transducer unit performs scanning operation by simultaneously transmitting a same number of ultrasonic beams in each of said plural angle regions.

5. An ultrasonic endoscopic apparatus according to claim 4, wherein said ultrasonic observation apparatus selectively supplies the drive signals to said ultrasonic transducer unit such that said ultrasonic transducer unit performs first scanning operation for selectively driving said plural ultrasonic transducers together with second scanning operation for steering an ultrasonic beam formed by ultrasonic waves transmitted from a predetermined number of ultrasonic transducers in each of said plural angle regions.

6. An ultrasonic endoscopic apparatus according to claim 5, wherein said ultrasonic observation apparatus selectively supplies the drive signals to said ultrasonic transducer unit such that said ultrasonic transducer unit performs first scanning operation for selectively driving said plural ultrasonic transducers together with second scanning operation for steering an ultrasonic beam formed by ultrasonic waves transmitted from a predetermined number of ultrasonic transducers in regions in which said first scanning operation is impossible.

7. An ultrasonic endoscopic apparatus according to claim 4, further comprising:
mode switching means for switching, in a Doppler mode in which plural ultrasonic pulses are continuously transmitted in each transmission direction, between a frame rate priority mode in which a number of continuous ultrasonic pulses are reduced within a predetermined range to increase a frame rate and a sensitivity priority mode in which the number of continuous ultrasonic pulses is larger than that in the frame rate priority mode to increase sensitivity.

8. An ultrasonic endoscopic apparatus according to claim 7, wherein said mode switching means is provided within said ultrasonic endoscope.

9. An ultrasonic endoscopic apparatus comprising:
an ultrasonic endoscope having an ultrasonic transducer unit including plural ultrasonic transducers, each having a first electrode and a second electrode, for transmitting and receiving ultrasonic waves, said plural ultrasonic transducers being provide in plural angle regions formed by dividing, a scanning angle region by a predetermined angle, each of said plural angle regions being divided into a first sub region and a second sub region, a plurality of first interconnections each connected to the first electrodes of a first respective one of said plural ultrasonic transducers provided in the first sub region an a second respective one of said plural ultrasonic transducers provided in the second sub region within corresponding one of said plural angle regions, and a plurality of second interconnections each connected to the second electrodes of ultrasonic transducers provided in respective one of the first sub regions and the second sub regions;
transmitting means for generating drive signals and supplying the drive signals to said ultrasonic transducer unit via said plurality of first interconnections;
plural pieces of switch means connected to said plurality of second interconnections and a fixed potential; and
control means for controlling said transmitting means such that scanning operation is performed by simultaneously transmitting a same number of ultrasonic beams in each of said plural angle regions and supplying control signals for controlling whether each of said plurality of second interconnections is connected to the fixed potential or not to said plural pieces of switch means.

10. An ultrasonic endoscopic apparatus according to claim 9, wherein:
each of said plural angle regions is divided into the first and second sub regions by a second predetermined angle; and
each of said plurality of first interconnections is connected to the first electrodes of the first respective one and the second respective one of said plural ultrasonic transducers located at said second predetermined angle.

11. An ultrasonic endoscopic apparatus according to claim 10, wherein:
said predetermined angle is 90°; and
said ultrasonic transducer unit performs scanning operation by simultaneously transmitting plural ultrasonic beams at an angle interval of 90° when selectively supplied with the drive signals via said plurality of first interconnections and said plurality of second interconnections.

12. An ultrasonic endoscopic apparatus according to claim 9, further comprising:

mode switching means for switching, in a Doppler mode in which plural ultrasonic pulses are continuously transmitted in each transmission direction, between a frame rate priority mode in which a number of continuous ultrasonic pulses are reduced within a predetermined range to increase a frame rate and a sensitivity priority mode in which the number of continuous ultrasonic pulses is larger than that in the frame rate priority mode to increase sensitivity.

13. An ultrasonic endoscopic apparatus according to claim 12, wherein said mode switching means is provided within said ultrasonic endoscope.

14. An ultrasonic endoscopic apparatus according to claim 9, wherein said plural pieces of switch means are provided within said ultrasonic endoscope.

* * * * *